United States Patent
Tani et al.

(10) Patent No.: US 9,687,600 B2
(45) Date of Patent: *Jun. 27, 2017

(54) INFUSION PREPARATION

(71) Applicant: OTSUKA PHARMACEUTICAL FACTORY, INC., Naruto-shi, Tokushima (JP)

(72) Inventors: Seiji Tani, Naruto (JP); Yasuhiro Mitsumoto, Naruto (JP)

(73) Assignee: OTSUKA PHARMACEUTICAL FACTORY, INC., Narturo-Shi, Tokushima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,534

(22) Filed: Dec. 18, 2015

(65) Prior Publication Data

US 2016/0101231 A1    Apr. 14, 2016

Related U.S. Application Data

(62) Division of application No. 13/990,018, filed as application No. PCT/JP2011/077392 on Nov. 28, 2011, now Pat. No. 9,446,184.

(30) Foreign Application Priority Data

Nov. 29, 2010  (JP) ................. 2010-265611

(51) Int. Cl.
| | |
|---|---|
| A61K 31/07 | (2006.01) |
| A61M 5/14 | (2006.01) |
| A61K 31/122 | (2006.01) |
| A61K 31/198 | (2006.01) |
| A61K 31/355 | (2006.01) |
| A61K 31/375 | (2006.01) |
| A61K 31/4415 | (2006.01) |
| A61K 31/51 | (2006.01) |
| A61K 31/525 | (2006.01) |
| A61K 31/593 | (2006.01) |
| A61K 31/714 | (2006.01) |
| A61K 33/14 | (2006.01) |
| A61K 45/06 | (2006.01) |
| A61J 1/20 | (2006.01) |
| A61K 9/00 | (2006.01) |

(52) U.S. Cl.
CPC .......... *A61M 5/1407* (2013.01); *A61J 1/2093* (2013.01); *A61K 9/0029* (2013.01); *A61K 31/07* (2013.01); *A61K 31/122* (2013.01); *A61K 31/198* (2013.01); *A61K 31/355* (2013.01); *A61K 31/375* (2013.01); *A61K 31/4415* (2013.01); *A61K 31/51* (2013.01); *A61K 31/525* (2013.01); *A61K 31/593* (2013.01); *A61K 31/714* (2013.01); *A61K 33/14* (2013.01); *A61K 45/06* (2013.01)

(58) Field of Classification Search
None
See application file for complete search history.

(56) References Cited

U.S. PATENT DOCUMENTS

| 5,728,681 A | 3/1998 | Kido et al. |
| 5,770,233 A | 6/1998 | Kido et al. |
| 6,541,029 B1 | 4/2003 | Namba et al. |

FOREIGN PATENT DOCUMENTS

| EP | 0 704 199 A1 | 4/1996 | | |
| EP | 0 752 243 A2 | 1/1997 | | |
| EP | 1 632 233 A1 | 3/2006 | | |
| JP | 06-209979 A | 8/1994 | | |
| JP | 08-000709 A | 1/1996 | | |
| JP | EP 0704199 A1 * | 4/1996 | ............ | A61J 1/2093 |
| JP | EP 0752243 A2 * | 1/1997 | ............ | A23L 1/296 |

(Continued)

OTHER PUBLICATIONS

Office Action dated May 2, 2014 in European Patent Application No. 11 84 5978.
Takashi Kuwahara, et al., "An Experimental Study on Phlebitic Potential of Amino Acid Solutions with Glucose and Electrolytes for Peripheral Parenteral Nutrition," Japanese Pharmacology and Therapeutics, 1996, pp. 2151-2157, vol. 24, No. 10.

(Continued)

*Primary Examiner* — Robert A Wax
*Assistant Examiner* — Melissa Mercier
(74) *Attorney, Agent, or Firm* — Sughrue Mion, PLLC

(57) ABSTRACT

An object of the present invention is to provide an infusion preparation in which the Maillard reaction between an amino acid and a reducing sugar does not occur during storage and the size of fat particles in the fat emulsion does not increase during storage, and in which various types of vitamins can be incorporated in a stable manner, in spite of the fact that it is a two-chamber infusion preparation. Furthermore, even if only one of the infusions (of the infusion preparation) is administered, the patient is unlikely to develop hyperkalemia, vascular pain, or phlebitis. The present invention provides an infusion preparation containing two chambers separated by a partition that can be communicably opened, wherein a first chamber contains a first-chamber infusion containing a sugar and a fat emulsion, a second chamber contains a second-chamber infusion containing an amino acid and an electrolyte, the first-chamber infusion is substantially free of potassium, and has a relative osmotic pressure of 2.0 to 3.0, the second-chamber infusion has a potassium concentration of 40 mEq/L or less and a relative osmotic pressure of 2.5 to 3.5, and a mixture of the first- and second-chamber infusions has a potassium concentration of 16 mEq/L or more as measured upon communicably opening the partition.

6 Claims, No Drawings

(56) References Cited

FOREIGN PATENT DOCUMENTS

| | | |
|---|---|---|
| JP | 2000-143509 A | 5/2000 |
| JP | 2001-328934 A | 11/2001 |
| JP | 2003-095937 A | 4/2003 |
| JP | 2004-189677 A | 7/2004 |
| JP | 2005-330244 A | 12/2006 |
| JP | 2007-137836 A | 6/2007 |

OTHER PUBLICATIONS

Office Action from the Japanese Patent Office issued Aug. 4, 2015 in counterpart Japanese Patent Application No. 2012-546860.

* cited by examiner

INFUSION PREPARATION

CROSS REFERENCE TO RELATED APPLICATIONS

This application is a divisional of U.S. application Ser. No. 13/990,018 filed Aug. 9, 2013, which is a National Stage of International Application No. PCT/JP2011/077392 filed Nov. 28, 2011, claiming priority based on Japanese Patent Application No. 2010-265611 filed Nov. 29, 2010, the contents of all of which are incorporated herein by reference in their entirety.

TECHNICAL FIELD

The present invention relates to an infusion preparation containing a sugar, a fat, an amino acid, and an electrolyte. More specifically, the present invention provides an infusion preparation, which is an infusion preparation (a high-calorie infusion preparation) contained in a two-chamber container, wherein a first chamber contains a sugar and a fat emulsion, and a second chamber contains an amino acid and an electrolyte.

BACKGROUND ART

An infusion preparation containing a sugar, an amino acid, and an electrolyte contained in an infusion bag having two chambers is known and widely used for the nutritional management of patients (see Non-Patent Literature 1).

Adding a reducing sugar and an amino acid to the same solution disadvantageously causes the Maillard reaction and modifies the solution. Therefore, in the infusion preparation, in order to prevent the Maillard reaction caused by a reducing sugar and an amino acid, an infusion containing a reducing sugar is placed in one chamber of an infusion bag, and an infusion containing an amino acid is separately placed in the other chamber. At the time of use, the infusions are mixed by bringing the two chambers into communication with each other and subsequently administered to the patient. In order to facilitate the mixing procedure, the two chambers are generally separated by a partition wall (for example, an easily peelable seal) that can be communicably opened at the time of use. However, there is a case where only one infusion is administered to the patient due to the omission of the communication procedure. Such an error often occurs. Therefore, when such an infusion preparation in a two-chamber container is used, it is very important to ensure that the patient is prevented from being adversely affected even in the case where only one infusion placed in one chamber is administered due to the omission of the communication procedure before use.

For example, when the potassium concentration in one infusion is relatively high, a patient may develop hyperkalemia if this infusion is singly administered thereto. In order to eliminate such a problem, an infusion preparation in which potassium is separately placed into the two chambers and the potassium concentration in each infusion is adjusted to 40 mEq/L or less has been examined (Patent Literature 1).

Further, particularly when an infusion is administered into a peripheral vein, if the osmotic pressure is too high, it may cause vascular pain or phlebitis. Therefore, it is considered to be desirable that an infusion have an appropriate osmotic pressure even before being mixed (Patent Literature 2).

Further, when an infusion preparation containing a sugar, an amino acid, and an electrolyte (a high-calorie infusion preparation) is singly administered for a long period of time, it may induce essential fatty acid deficiency. The development of essential fatty acid deficiency can be prevented by the administration of a fat emulsion in combination with a high-calorie infusion preparation. Further, fat has a high calorific value per weight, and also has advantages such as the fact that, unlike sugar, it does not cause osmotic diuresis. However, when a long time has elapsed after an electrolyte infusion and a fat emulsion were mixed together, the size of fat droplets becomes large, leading to the risk of causing fat embolism when such a mixture is administered. Therefore, an infusion preparation in a two-chamber container in which a fat emulsion and an electrolyte are placed in different chambers and mixed at the time of administration has been developed.

Still further, it is known that acidosis may occur when a vitamin B1 deficiency occurs during the administration of a high-calorie infusion, and vitamin supplementation is required to prevent such a risk when administering a high-calorie infusion. In order to avoid such a problem, a high-calorie infusion preparation comprising three liquids (liquids in large, medium, and small chambers) to which vitamins, in addition to a sugar, an amino acid, and an electrolyte, are added in advance has been developed (for example, the Fulcaliq infusion preparation). The high-calorie infusion preparation is prepared in a form that contains infusions having different compositions in large, medium, and small chambers, in view of problems in the stability of vitamins (particularly fat-soluble vitamins). However, infusion preparations having three chambers require additional work during production and use, thus creating problems with production cost and use. Further, for example, the package insert for the Fulcaliq infusion preparation instructs the user not to mix a fat emulsion as a precaution during preparation.

As described above, techniques that have been examined with respect to various problems are useful in solving the respective problems; however, an infusion preparation that has solved all of the problems was yet to be developed.

CITATION LIST

Patent Literature

PTL 1: Japanese Unexamined Patent Publication No. 2004-189677
PTL 2: Japanese Unexamined Patent Publication No. 2003-95937

Non-Patent Literature

NPL 1: Japanese Pharmacology & Therapeutics, 24(10), 2151 (1996)

Technical Problems

An object of the present invention is to develop an infusion preparation that can solve all of the above problems.

Solution to Problems

The present inventors surprisingly found that the following advantages can be achieved by using an infusion preparation comprising two chambers separated by a partition that can be communicably opened, wherein a first chamber contains a first-chamber infusion comprising a sugar and a fat emulsion, a second chamber contains a second-chamber infusion comprising an amino acid and an electrolyte, the first-chamber infusion is substantially free of potassium and has a relative osmotic pressure of 2.0 to 3.0, the second-chamber infusion has a potassium concentration of 40 mEq/L or less and a relative osmotic pressure of 2.5 to 3.5, and a mixture of the first- and second-chamber infusions has a potassium concentration of 16 mEq/L or more as measured upon communicably opening the partition. In this infusion preparation, the Maillard reaction between an amino acid and a reducing sugar does not occur during storage, and the size of fat particles in the fat emulsion does not increase during storage. Even if only one of the infusions is administered, the patient is unlikely to develop hyperkalemia, vascular pain, or phlebitis. In spite of the fact that it is a two-chamber infusion preparation, various types of vitamins can be incorporated in a stable manner. The present inventors made further improvements, and finally accomplished the present invention.

More specifically, the present invention includes the infusion preparations itemized below.

Item 1. An infusion preparation comprising two chambers separated by a partition that can be communicably opened, wherein
a first chamber contains a first-chamber infusion comprising a sugar and a fat emulsion;
a second chamber contains a second-chamber infusion comprising an amino acid and an electrolyte;
the first-chamber infusion is substantially free of potassium, and has a relative osmotic pressure of 2.0 to 3.0;
the second-chamber infusion has a potassium concentration of 40 mEq/L or less and a relative osmotic pressure of 2.5 to 3.5;
and a mixture of the first- and second-chamber infusions has a potassium concentration of 16 mEq/L or more as measured upon communicably opening the partition.

Item 2. The infusion preparation according to Item 1 wherein the first-chamber infusion has a pH of 4.5 to 6.5, and the second-chamber infusion has a pH of 6.0 to 7.4.

Item 3. The infusion preparation according to Item 1 or 2, wherein the volume ratio of the first-chamber infusion to the second-chamber infusion is 3:2 to 3:5.

Item 4. The infusion preparation according to any one of Items 1 to 3, wherein the first chamber further contains vitamin B1.

Item 5. The infusion preparation according to Item 4 wherein the first-chamber infusion further contains vitamin A, vitamin B6, vitamin B12, vitamin D, vitamin E, and vitamin K, and the second-chamber infusion further contains vitamin C and vitamin B2.

Advantageous Effects of Invention

The infusion preparation of the present invention solves all of the above problems. In the infusion preparation, the Maillard reaction between an amino acid and a reducing sugar does not occur during storage, and the size of fat particles in the fat emulsion does not increase during storage. Furthermore, even if only one of the infusions is administered, the patient is unlikely to develop hyperkalemia, vascular pain, or phlebitis. Furthermore, vitamin B1 incorporated is expected to inhibit the onset of acidosis. Moreover, because the infusion preparation is contained in a two-chamber container in which other vitamins, such as lipid soluble vitamins, can be incorporated, the time and labor required in the manufacturing process and use can be reduced.

DESCRIPTION OF EMBODIMENTS

The present invention is described below in more detail.

The present invention provides an infusion preparation comprising two chambers separated by a partition that can be communicably opened, wherein a first chamber contains a first-chamber infusion comprising a sugar and a fat emulsion, and a second chamber contains a second-chamber infusion comprising an amino acid and an electrolyte.

First-Chamber Infusion

The first-chamber infusion used in the present invention comprises a sugar and a fat emulsion.

Examples of sugars that can be incorporated in the first-chamber infusion include reducing sugars such as glucose, fructose, and maltose; non-reducing sugars such as xylitol, sorbitol and glycerol; etc. Among these sugars, reducing sugars are preferable, and glucose is particularly preferable, from the viewpoint of blood glucose level management, etc. Such sugars may be used singly or in a combination of two or more.

The amount of sugar in the first-chamber infusion is preferably in the range of 70 to 150 g/L. In the infusion preparation of the present invention, the mixture of the first- and second-chamber infusions may preferably have a sugar concentration of 50 to 100 g/L, and more preferably 50 to 75 g/L.

To prevent the onset of acidosis during infusion therapy, vitamin B1 is preferably incorporated in the first-chamber infusion. Examples of vitamin B1 that can be incorporated in the first-chamber infusion include thiamine chloride hydrochloride, thiamine mononitrate, prosultiamine, octotiamine, and the like.

The amount of vitamin B1 in the first-chamber infusion may be, for example, in the range of 1.5 to 10 mg/L, and preferably 2 to 8 mg/L, based on thiamine. In the infusion preparation of the present invention, the mixture of the first- and second-chamber infusions preferably has a vitamin B1 concentration of 1 to 6 mg/L, and more preferably 1.5 to 4 mg/L.

The fat emulsion incorporated in the first-chamber infusion is an oil-in-water emulsion produced by dispersing an oil and/or fat in water using an emulsifying agent. The fat emulsion can be produced according to a usual method. For example, after an oil and/or fat, and an emulsifying agent are added to water, the mixture is stirred to prepare a crude emulsion. Subsequently, the crude emulsion is emulsified by a conventional method, such as a high-pressure emulsification method.

Examples of oils and fats that can be preferably used include edible oils. Specific examples thereof include vegetable oils (e.g., soybean oil, olive oil, cottonseed oil, safflower oil, corn oil, coconut oil, and perilla oil); fish oils (e.g., cod liver oil); medium-chain fatty acid triglycerides ($C_{8-10}$ fatty acid triglycerides) (e.g., product name: PANACET (produced by NOF Corporation), ODO (produced by Nisshin Oil Mills, Ltd.), COCONARD (produced by Kao Corporation), Miglyol (produced by Mitsuba Trading Co., Ltd.)); synthetic triglycerides (e.g., 2-linoleoyl-1,3-dioctanoyl glycerol (8L8), and 2-linoleoyl-1,3-didecanoyl-glycerol (10L10)); and the like. Such oils and fats may be used singly or in a combination of two or more.

The emulsifying agent may be selected from, for example, various pharmaceutically acceptable emulsifying agents. Specific examples thereof include egg yolk phospholipid (egg yolk lecithin), hydrogenated yolk phospholipid, soybean phospholipid (soybean lecithin), hydrogenated soybean phospholipid; nonionic surfactants; and the like. Such emulsifiers may be used singly or in a combination of two or more.

Soybean oil is particularly preferable as an oil and/or fat. Egg-yolk phospholipid (egg yolk lecithin) is particularly preferable as an emulsifying agent. Lecithin, such as egg yolk lecithin, is particularly preferable because it can also act as a phosphorus source, as described below.

Insofar as an oil-in-water fat emulsion can be produced, the amounts of oil and/or fat and emulsifier used to prepare the fat emulsion are not particularly limited. The oil and/or fat is typically used in such an amount as to achieve a concentration of about 0.5 to 6 w/v %, and preferably about 1 to 5 w/v %, in the obtained fat emulsion. Furthermore, the emulsifying agent is typically used in such an amount as to achieve a concentration of about 0.01 to 2 w/v %, and more preferably about 0.05 to 1 w/v %, in the obtained fat emulsion.

One example of a particularly preferable method for producing the fat emulsion according to the present invention is described below. More specifically, an oil and/or fat and an emulsifying agent are added to water, and at least one member selected from glycerol and glucose is also added thereto. The mixture is then stirred to prepare a crude emulsion. Subsequently, the crude emulsion is emulsified by a conventional method, such as a high-pressure emulsification method. The high-pressure emulsification method may be carried out, for example, by passing the crude emulsion through an emulsifier, such as a Manton Gaulin homogenizer, at a rate of 20 to 700 kg/cm$^2$ about 2 to 50 times, and preferably 3 to 20 times. In this method, insofar as glycerol and/or glucose is present during the emulsification, the manner and timing of addition thereof are not limited. For example, glycerol and/or glucose may be added to the crude emulsion prepared by using an oil and/or fat and an emulsifying agent, and the resulting crude emulsion may be emulsified. The glycerol and/or glucose is typically used in such an amount as to achieve a concentration of about 30 to 70 w/v %, and preferably about 40 to 60 w/v %, in the obtained fat emulsion.

If necessary, various additives that are known to be added to fat emulsions may be further incorporated. Examples of such additives include pH adjusters. Specific examples of pH adjusters include acids such as hydrochloric acid; alkalis such as sodium hydroxide and potassium hydroxide; and organic acids and amino acids. Examples of organic acids include acetic acid, lactic acid, citric acid, malic acid, succinic acid, and the like. Examples of amino acids include L-histidine, L-lysine, and the like. Among these, oil-soluble materials may be premixed into an oily component of the emulsion. Water-soluble materials may be mixed into water for injection, or added to an aqueous phase of the obtained fat emulsion. The amounts of additives to be used can be suitably determined, and may be the same as conventionally known amounts.

The fat emulsion is incorporated in the first-chamber infusion in an amount of 0.5 to 6 w/v %, preferably 1 to 5 w/v %, and more preferably 2 to 5 w/v %, based on oils and fats. In the infusion preparation of the present invention, the mixture of the first- and second-chamber infusions contains the fat emulsion in a concentration of 0.25 to 6 w/v %, preferably 0.5 to 3 w/v %, and more preferably 1 to 2.5 w/v %, based on oils and fats.

The first-chamber infusion has a pH in the range of 4.5 to 6.5, and preferably 5.0 to 6.5. When the pH is within the above-mentioned range, the fat emulsion and vitamin B in the first-chamber infusion can be stabilized. The pH of the first-chamber infusion can be adjusted by using a pH adjuster, such as hydrochloric acid, acetic acid, glacial acetic acid, lactic acid, malic acid, citric acid, sodium hydroxide, or potassium hydroxide. L-histidine may also be used as a pH adjuster.

In view of enhancing the stability of vitamin B1, the first-chamber infusion preferably has a titratable acidity of 1 or less. The titratable acidity refers to an amount (mL) of a 0.1 mol/L sodium hydroxide aqueous solution required to neutralize 100 ml of a solution to pH 7.4.

Distilled water for injection can be typically used as a solvent of the first-chamber infusion.

In the infusion preparation of the present invention, the fluid volume of the first-chamber infusion is suitably determined according to the total fluid volume of the infusion preparation and the fluid volume of the second-chamber infusion.

The first-chamber infusion is substantially free of potassium. The phrase "substantially free of potassium" means that no potassium-containing compounds are added.

The first-chamber infusion has a relative osmotic pressure of about 2.0 to 3.0. The relative osmotic pressure as used herein refers to a ratio relative to the osmotic pressure of physiological saline (i.e., a relative ratio, with the osmotic pressure of physiological saline defined as 1). The relative osmotic pressure of the infusion refers to a ratio relative to the osmotic pressure of physiological saline, unless otherwise specified.

Second-Chamber Infusion

The second-chamber infusion used in the present invention contains an amino acid and an electrolyte.

Any amino acid that can be incorporated in amino acid infusions for the purpose of nutritional supplementation for the body may be used as an amino acid to be contained in the second-chamber infusion. In the present invention, the amino acid is typically used in the form of a free amino acid. However, the amino acid may also be used in the form of a pharmaceutically acceptable salt, an ester, a N-acyl derivative, or a dipeptide. Examples of free amino acids that can be incorporated in the second-chamber infusion include L-leucine, L-isoleucine, L-valine, L-lysine, L-threonine, L-tryptophan, L-methionine, L-phenylalanine, L-cysteine, L-tyrosine, L-arginine, L-histidine, L-alanine, L-proline, L-serine, glycine, L-aspartic acid, L-glutamic acid, and the like. Examples of amino acid salts include inorganic acid salts such as L-arginine hydrochloride, L-cysteine hydrochloride, L-glutamic acid hydrochloride, L-histidine hydrochloride, and L-lysine hydrochloride; organic acid salts such as L-lysine acetate and L-lysine malate; etc. Examples of amino acid esters include L-tyrosine methyl ester, L-methionine methyl ester, L-methionine ethyl ester, and the like. Examples of N-acyl amino acids include N-acetyl-L-cysteine, N-acetyl-L-tryptophan, N-acetyl-L-proline, and the like. Examples of amino acid dipeptides include L-tyrosyl-L-tyrosine, L-alanyl-L-tyrosine, L-arginyl-L-tyrosine, L-tyrosyl-L-arginine, and the like. In particular, L-cysteine is preferably incorporated in the form of acetylcysteine in view of stability. Such amino acids may be used singly, but are preferably used in a combination of two or more, from the viewpoint of nutritional supplementation. For example, it is preferable to incorporate at least all of the essential amino acids (i.e., 9 types of amino acids: L-leucine, L-isoleucine, L-valine, L-lysine, L-threonine, L-tryptophan, L-methionine, L-phenylalanine, and L-histidine).

The amount of amino acids in the second-chamber infusion may be, for example, preferably 40 to 120 g/L, and more preferably 50 to 100 g/L, based on the total amount of free amino acids. In the infusion preparation of the present invention, the mixture of the first- and second-chamber infusions preferably has an amino acid concentration of 10 to 50 g/L, and more preferably 20 to 30 g/L, based on the total amount of free amino acids.

A preferable combination of amino acids to be incorporated in the second-chamber infusion, and proportions thereof are, for example, as follows, in terms of free amino acids: L-leucine: 5 to 15 g/L; L-isoleucine: 3 to 9 g/L; L-valine: 3 to 9 g/L; L-lysine: 3 to 12 g/L; L-threonine: 1.2 to 6 g/L; L-tryptophan: 0.3 to 3 g/L; L-methionine: 0.6 to 4.8 g/L; L-phenylalanine: 1.8 to 9 g/L; L-cysteine: 0.1 to 1.8 g/L; L-tyrosine: 0.06 to 1.2 g/L; L-arginine: 3 to 12 g/L; L-histidine: 1.2 to 6 g/L; L-alanine: 3 to 9 g/L; L-proline: 1.2 to 6 g/L; L-serine: 0.6 to 4.2 g/L; glycine: 1.2 to 6 g/L; L-aspartic acid: 0.12 to 1.8 g/L; and L-glutamic acid: 0.12 to 1.8 g/L.

In the infusion preparation of the present invention, the mixture of the first- and second-chamber infusions preferably contains amino acids in the following concentrations, in terms of free amino acids: L-leucine: 3 to 9 g/L; L-isoleucine: 1.5 to 4.5 g/L; L-valine: 1.5 to 4.5 g/L; L-lysine: 1.5 to 5 g/L; L-threonine: 0.6 to 3 g/L; L-tryptophan: 0.15 to 1.5 g/L; L-methionine: 0.3 to 2.4 g/L; L-phenylalanine: 0.85 to 4.5 g/L; L-cysteine: 0.03 to 0.9 g/L; L-tyrosine: 0.03 to 0.6 g/L; L-arginine: 1.5 to 5 g/L; L-histidine: 0.6 to 3 g/L; L-alanine: 1.5 to 4.5 g/L; L-proline: 0.6 to 3 g/L; L-serine: 0.3 to 2.1 g/L; glycine: 0.6 to 3 g/L; L-aspartic acid: 0.06 to 0.9 g/L; and L-glutamic acid: 0.06 to 0.9 g/L.

The electrolyte to be incorporated in the second-chamber infusion is an electrolyte that is used in the infusion field. More specifically, it is an electrolyte contained in a body fluid (body fluid electrolyte) (e.g., blood and intracellular fluid), which can be said to be a physiologically important electrolyte. Specific examples of such electrolytes include potassium, calcium, sodium, magnesium, phosphorus, zinc, chlorine, and the like. In the infusion preparation of the present invention, it is preferable that such an electrolyte not be incorporated in the first-chamber infusion. In particular, although potassium is usually incorporated in both infusions of a two-chamber infusion preparation in order to avoid the risk of administering a high concentration of potassium, potassium is incorporated only in the second-chamber infusion according to the infusion preparation of the present invention.

Examples of potassium sources include potassium chloride, potassium acetate, potassium citrate, potassium glycerophosphate, potassium sulfate, potassium lactate, and the like. Among these, potassium glycerophosphate is preferable because it also acts as a phosphorus source. Such potassium sources may be in the form of a hydrate. Potassium is incorporated in such an amount as to achieve a concentration of mEq/L or less (preferably 25 to 40 mEq/L) in the second-chamber infusion. In the infusion preparation of the invention, the mixture of the first- and second-chamber infusions has a potassium concentration of 16 mEq/L or more (preferably 16 to 25 mEq/L), and more preferably 16 to 20 mEq/L.

Examples of calcium sources include calcium salts such as calcium gluconate, calcium chloride, calcium glycerophosphate, calcium lactate, calcium pantothenate, and calcium acetate. Calcium salts may be in the form of a hydrate (e.g., calcium gluconate hydrate). Calcium is incorporated in such an amount as to achieve a concentration of 15 mEq/L or less (preferably 6 to 12 mEq/L) in the second-chamber infusion. In the infusion preparation of the invention, the mixture of first- and second-chamber infusions has a calcium concentration of 9 mEq/L or less (preferably 3 to 6 mEq/L).

Examples of sodium sources include sodium salts such as sodium chloride, sodium lactate, sodium acetate, sodium sulfate, sodium glycerophosphate, sodium citrate, and sodium lactate. When phosphorus, and calcium and/or magnesium are incorporated in the infusion preparation of the present invention, sodium citrate is preferably used as a sodium source in order to prevent precipitation of these elements. Sodium sources may be in the form of a hydrate. Sodium is incorporated in the second-chamber infusion in a concentration of 50 to 100 mEq/L, and preferably 40 to 80 mEq/L in the second-chamber infusion. In the infusion preparation of the present invention, the mixture of the first- and second-chamber infusions preferably has a sodium concentration of 25 to 50 mEq/L, and preferably 30 to 40 mEq/L.

Examples of magnesium sources include magnesium sulfate, magnesium chloride, magnesium acetate, and the like. Magnesium sources may be in the form of a hydrate. The amount of magnesium in the second-chamber infusion may be, for example, 1 to 20 mEq/L, and preferably 5 to 15 mEq/L, in the second-chamber infusion. In the infusion preparation of the present invention, the mixture of the first- and second-chamber infusions preferably has a magnesium concentration of 0.5 to 10 mEq/L, and preferably 2 to 6 mEq/L.

When an inorganic salt is used as a phosphorus source, calcium phosphate and magnesium phosphate may precipitate. Accordingly, an organic salt, such as sodium glycerophosphate or potassium glycerophosphate, is preferably used. When lecithin is used as an emulsifying agent in the first chamber, the lecithin also acts as a phosphorus source. When the phosphorus derived from lecithin can provide a sufficient amount of phosphorus, it is unnecessary to incorporate phosphorus in the second chamber, and no precipitation of calcium phosphate, etc., occurs, which is preferable. The amount of phosphorus in the second-chamber infusion may be, for example, 0 to 20 mmol/L. In the infusion preparation of the invention, the mixture of the first- and second-chamber infusions preferably has a phosphorus concentration of 1 to 20 mmol/L, and more preferably 5 to 10 mmol/L.

Examples of zinc sources include zinc sulfate, zinc chloride, and the like. Zinc sources may be in the form of a hydrate. The amount of zinc in the second-chamber infusion is 2.5 to 15 μmol/L. In the infusion preparation of the invention, the mixture of the first- and second-chamber infusions preferably has a zinc concentration of 1.5 to 9 μmol/L.

Examples of chlorine sources include sodium chloride, potassium chloride, magnesium chloride, calcium chloride, and the like. The amount of chlorine in the second-chamber infusion may be, for example, 50 to 100 mEq/L, and preferably 40 to 80 mEq/L. In the infusion preparation of the present invention, the mixture of the first- and second-chamber infusions preferably has a chlorine concentration of 25 to 60 mEq/L, and more preferably 30 to 40 mEq/L.

The pH of the second-chamber infusion is preferably adjusted to 6.0 to 7.4, and preferably 6.5 to 7.2, by using a pH adjuster, if necessary. Examples of pH adjusters that can be used may be the same as mentioned above for the first-chamber infusion. In particular, the use of citric acid is preferable because it can inhibit the precipitation of calcium phosphate. When the second-chamber infusion has a pH within the above-mentioned range, amino acids that are prone to undergo chemical changes, such as L-cysteine and L-glutamic acid, can be stabilized. Furthermore, the pH of the mixture of the second-chamber infusion with the first-chamber infusion can be maintained in the optimum range as described below.

As a solvent in the second-chamber infusion, distilled water for injection can be typically used.

In the infusion preparation of the present invention, the second-chamber infusion has a relative osmotic pressure of about 2.5 to 3.5.

If necessary, the infusion preparation of the present invention may contain a stabilizer. Examples of stabilizers that can be incorporated in the infusion preparation of the present invention include sulfites such as sodium bisulfite. To avoid the decomposition of vitamin B1 contained in the first-chamber infusion, sulfite is incorporated in the second-chamber infusion. The amount of sulfite in the second-chamber infusion may be, for example, 20 to 50 mg/L.

In addition to vitamin B1, various other types of vitamins can be added to the infusion preparation of the present invention. Various types of vitamins can be stably added to the infusion preparation in the two-chamber container without the need to place the infusion preparation in a three- or four-chamber container. This is one of the features of the infusion preparation of the present invention. Vitamins are classified into water-soluble vitamins and fat-soluble vitamins. In the infusion preparation of the present invention, a fat-soluble vitamin is added to the first-chamber infusion. Further, a water-soluble vitamin may be added to either the first- or second-chamber infusion. However, as described above, vitamin B1 is added to the first-chamber infusion.

Examples of water-soluble vitamins added to the infusion preparation of the present invention include B-complex vitamins and vitamin C. In addition to vitamin B1 (thiamine), examples of B-complex vitamins include vitamin B2 (riboflavin), vitamin B3 (niacin), vitamin B5 (pantothenic acid), vitamin B6, vitamin B7 (biotin), vitamin B9 (folic acid), and vitamin B12 (cyanocobalamin). Further, examples of fat-soluble vitamins include vitamin A, vitamin D (in particular, cholecalciferol), vitamin E, and vitamin K.

When vitamin C (ascorbic acid) is added, it can be added to either or both of the first- and second-chamber infusions. However, it is preferably added to the second-chamber infusion. When vitamin C is added to the second-chamber infusion, the amount of vitamin C in the second-chamber infusion is, for example, 50 to 500 mg/L, and preferably 100 to 400 mg/L. Further, in the infusion preparation of the present invention, the vitamin C concentration in the mixture of the first- and second-chamber infusions is preferably set to satisfy the following ranges: generally 25 to 250 mg/L, preferably 50 to 200 mg/L, and more preferably 40 to 100 mg/L.

As vitamin B2, riboflavin, riboflavin sodium phosphate, flavin mononucleotide, and the like can be used. When vitamin B2 is added, it can be added to either or both of the first- and second-chamber infusions. However, vitamin B2 and folic acid are preferably placed in different chambers in order to prevent the destabilization of folic acid caused by a reaction between vitamin B2 and folic acid. For example, when folic acid is added to the first-chamber infusion, vitamin B2 is preferably added to the second-chamber infusion. When vitamin B2 is added to the second-chamber infusion, the amount of vitamin B2 in the second-chamber infusion is, for example, generally 2.5 to 15 mg/L, and preferably 4 to 8 mg/L, in terms of riboflavin. Further, in the infusion preparation of the present invention, the vitamin B2 concentration in the mixture of the first- and second-chamber infusions is preferably set to satisfy the following ranges: generally 0.5 to 10 mg/L, and preferably 0.5 to 3 mg/L, in terms of riboflavin.

As vitamin B6, pyridoxine, salts of pyridoxine such as pyridoxine hydrochloride, and the like can be used. When vitamin B6 is added, it can be added to either or both of the first- and second-chamber infusions. However, vitamin B6 becomes very unstable to light when it coexists with vitamin B2. Therefore, vitamin B6 is preferably added to the infusion to which vitamin B2 is not added. When vitamin B6 is added to the first-chamber infusion, the amount of vitamin B6 in the first-chamber infusion is, for example, generally 2 to 10 mg/L, and preferably 2.5 to 5 mg/L, in terms of pyridoxine. Further, in the infusion preparation of the present invention, the vitamin B6 concentration in the mixture of the first- and second-chamber infusions is preferably set to satisfy the following ranges: generally 1 to 10 mg/L, and preferably 1.5 to 3.5 mg/L, in terms of pyridoxine.

When folic acid is added, it can be added to either or both of the first- and second-chamber infusions; however, it is preferably added to the first-chamber infusion. When folic acid is added to the first-chamber infusion, the amount of folic acid in the first-chamber infusion is, for example, generally 0.1 to 0.8 mg/L, and preferably 0.2 to 0.5 mg/L. Further, in the infusion preparation of the present invention, the folic acid concentration in the mixture of the first- and second-chamber infusions is preferably set to satisfy the following ranges: generally 0.1 to 0.7 mg/L, and preferably 0.2 to 0.4 mg/L.

As vitamin B12, cyanocobalamin, hydroxocobalamin acetate, methylcobalamin, and the like can be used. When vitamin B12 is added, it can be added to either or both of the first- and second-chamber infusions; however, it is preferably added to the first-chamber infusion. When vitamin B12 is added to the first-chamber infusion, the amount of vitamin B12 in the first-chamber infusion is, for example, 2 to 10 µg/L, and preferably 2.5 to 5 µg/L. Further, in the infusion preparation of the present invention, the vitamin B12 concentration in the mixture of the first- and second-chamber infusions is preferably set to satisfy the following ranges: generally 0.5 to 10 mg/L, and preferably 0.5 to 3 mg/L.

As niacin, for example, nicotinamide can be preferably used. When niacin is added, it can be added to either or both of the first- and second-chamber infusions; however, it is preferably added to the second-chamber infusion. When niacin is added to the second-chamber infusion, the amount of niacin in the second-chamber infusion is, for example, 10 to 100 mg/L, and preferably 20 to 50 mg/L. Further, in the infusion preparation of the present invention, the niacin concentration in the mixture of the first- and second-chamber infusions is preferably set to satisfy the following ranges: generally 5 to 50 mg/L, and preferably 5 to 20 mg/L.

As pantothenic acid, panthenol can be preferably used. When pantothenic acid is added, it can be added to either or both of the first- and second-chamber infusions; however, it is preferably added to the second-chamber infusion. When pantothenic acid is added to the second-chamber infusion, the amount of pantothenic acid in the second-chamber infusion is, for example, to 30 mg/L, and preferably 10 to 20 mg/L, in the case of panthenol. Further, in the infusion preparation of the present invention, the panthenol concentration in the mixture of the first- and second-chamber infusions is preferably set to satisfy the following ranges: generally 2.5 to 15 mg/L, and preferably 5 to 10 mg/L.

When biotin is added, it can be added to either or both of the first- and second-chamber infusions; however, it is preferably added to the second-chamber infusion. When biotin is added to the second-chamber infusion, the amount of biotin in the second-chamber infusion is, for example, 10 to 100 µg/L, and preferably 20 to 80 µg/L. Further, in the infusion preparation of the present invention, the biotin concentration in the mixture of the first- and second-chamber infusions is preferably set to satisfy the following ranges: generally 1 to 50 µg/L, and preferably 10 to 40 µg/L.

As vitamin A, retinol palmitate can be preferably used. Further, vitamin A oil formed by dissolving retinol palmitate in oil can also be used. Vitamin A is fat-soluble, and is added to the first-chamber infusion. The amount of vitamin A in the first-chamber infusion is, for example, 1,000 to 5,000 IU/L, and preferably 2,000 to 4,000 IU/L. Further, in the infusion preparation of the present invention, the vitamin A concentration in the mixture of the first- and second-chamber infusions is preferably set to satisfy the following ranges: generally 500 to 2,500 IU/L, and preferably 1,000 to 2,000 IU/L. IU stands for International Unit. It is also called vitamin A unit.

As vitamin D, cholecalciferol (vitamin $D_3$) can be preferably used. Vitamin D is fat-soluble, and is added to the first-chamber infusion. The amount of vitamin D in the first-chamber infusion is, for example, 2 to 10 µg/L, and preferably 2.5 to 5 µg/L. Further, in the infusion preparation of the present invention, the vitamin D concentration in the mixture of the first- and second-chamber infusions is preferably set to satisfy the following ranges: generally 0.5 to 10 µg/L, and preferably 0.5 to 3 µg/L.

As vitamin E, tocopherol acetate can be preferably used. Vitamin E is fat-soluble, and is added to the first-chamber infusion. The amount of vitamin E in the first-chamber infusion is, for example, 2 to 50 mg/L, and preferably 5 to 20 mg/L. Further, in the infusion preparation of the present invention, the vitamin D concentration in the mixture of the first- and second-chamber infusions is preferably set to satisfy the following ranges: generally 1 to 25 mg/L, and preferably 2.5 to 10 mg/L.

As vitamin K, phytonadione (vitamin $K_1$) can be preferably used. Vitamin K is fat-soluble, and is added to the first-chamber infusion. The amount of vitamin K in the first-chamber infusion is, for example, 50 to 2,500 µg/L, and preferably 80 to 2,000 µg/L. Further, in the infusion preparation of the present invention, the vitamin K concentration in the mixture of the first- and second-chamber infusions is preferably set to satisfy the following ranges: generally 20 to 1,200 µg/L, and preferably 30 to 1,000 µg/L.

A preferable example of the first- and second-chamber infusion compositions is shown below.
First-Chamber Infusion
Purified soybean oil: 10-50 g/L
Glucose: 70-150 g/L
Thiamine chloride hydrochloride: 3-10 mg/L
Pyridoxine hydrochloride: 3-7 mg/L
Cyanocobalamin: 2.5-5 µg/L
Folic acid: 0.2-0.5 mg/L
Vitamin A oil: 2,000-4,000 IU/L
Cholecalciferol: 2.5-5 µg/L
Tocopherol acetate: 5-20 mg/L
Phytonadione: 80-2,000 µg/L
Second-Chamber Infusion
L-leucine: 5-15 g/L
L-isoleucine: 3-9 g/L
L-valine: 3-9 g/L
L-lysine hydrochloride: 3.5-15 g/L
L-threonine: 1.2-6 g/L
L-tryptophan: 0.3-3 g/L
L-methionine: 0.6-4.8 g/L
Acetylcysteine: 0.13-2.4 g/L
L-phenylalanine: 1.8-9 g/L
L-tyrosine: 0.06-1.2 g/L
L-arginine: 3-12 g/L
L-histidine: 1.2-6 g/L
L-alanine: 3-9 g/L
L-proline: 1.2-6 g/L
L-serine: 0.6-4.2 g/L
Glycine: 1.2-6 g/L
L-asparatic acid: 0.12-1.8 g/L
L-glutamic acid: 0.12-1.8 g/L
Sodium: 40-80 mEq/L
Potassium: 25-40 mEq/L
Calcium: 6-12 mEq/L
Magnesium: 5-15 mEq/L
Chlorine: 40-80 mEq/L
Phosphorus: 0-20 mmoL/L
Zinc: 2.5-15 µmol/L
Riboflavin Sodium Phosphate: 5-10 mg/L
Ascorbic acid: 0.1-0.4 g/L
Biotin: 20-80 µg/L
Nicotinamide: 20-50 mg/L
Panthenol: 9-19 mg/L Both of the first- and second chamber infusions can be produced by a known method for producing infusions. For example, the first- and second chamber infusions can be produced by dissolving each of the above-described infusion components in distilled water for injection. Fat-soluble components are preferably used, for example, after being emulsified as described above.

Mixture of the First- and Second-Chamber Infusions

The infusion preparation of the present invention is used by mixing the first-chamber infusion and the second-chamber infusion at the time of use. In order to improve the safety by suppressing the occurrence of vascular pain and phlebitis, it is desirable that the mixture of the first- and second-chamber infusions have a pH of 6 to 7.4, and preferably 6.5 to 7.0, a titratable acidity of 1 to 10, and a relative osmotic pressure of 2 to 3.

Further, in the infusion preparation of the present invention, the volume ratio between the first-chamber infusion and the second-chamber infusion is suitably determined according to the above-described amount of the first- and second-chamber infusions and the like. In view of the stability of each component contained and the osmotic pressure setting in each chamber, the volume ratio (first-chamber infusion:second-chamber infusion) is, for example, 3:2-3:5.

Further, the calorific value of the mixture is preferably 450 to 750 kcal/L, more preferably 500 to 650 kcal/L. In this calorific value, the percentage of fat is preferably 40% or less, and more preferably 20 to 40%. Further, in this calorific value, the percentages of sugar, fat, and amino acid are preferably as follows: 40 to 60% of sugar; 20 to 40% of fat; and 10 to 30% of amino acid, and more preferably, 45 to 55% of sugar; 25 to 35% of fat; and 15 to 25% of amino acid.

An approximate calorific value of each component can be determined by multiplying the amount (g) by 4 for sugar, by 9 for fat, and by 4 for amino acid. Specifically, the calorific value of sugar is about 4 kcal/g, the calorific value of fat is about 9 kcal/g, and the calorific value of amino acid is about 4 kcal/g. An approximate calorific value can be determined based on this information. The calorific value of the mixture described above is based on a value calculated by the above formula.

A preferable example of the composition of each component in the mixture is shown below.

TABLE 1

| | Components | Amount (1,000 mL) | |
|---|---|---|---|
| Electrolytes | Na | 35 | mEq |
| | K | 20 | mEq |
| | Ma | 5 | mEq |
| | Ca | 5 | mEq |
| | Cl | 35 | mEq |
| | P | 10 | mmol |
| | Zn | 5 | µmol |
| Sugar | Glucose | 75 | g |
| Fat | Purified soybean oil | 20 | g |
| Amino acid | Amino acid | 30 | g |
| Vitamins | Thiamine chloride hydrochloride | 1.9 | mg |
| | Riboflavin sodium phosphate | 2.3 | mg |
| | Pyridoxine hydrochloride | 2.45 | mg |
| | Cyanocobalamin | 2.5 | µg |
| | Nicotinamide | 20 | mg |
| | Panthenol | 7 | mg |
| | Folic acid | 0.2 | mg |
| | Biotin | 30 | µg |
| | Ascorbic acid | 50 | mg |
| | Vitamin A oil | 1,650 | IU |
| | Cholecalciferol | 2.5 | µg |
| | Tocopherol acetate | 5 | mg |
| | Phytonadione | 1 | mg |

Infusion Preparation Usage Form

The infusion preparation of the present invention is used in order to manage the nutrition of a perioperative patient when the patient has mild hypoproteinemia or mild malnutrition due to inadequate oral intake or when the patient is in the invasive phase. In particular, the infusion preparation is suitably used to manage the nutrition of a patient having difficulty receiving oral nutritional support in the postoperative period or due to a digestive disorder and the like (preferably, a patient who has undergone gastric resection surgery). The infusion preparation of the present invention is administered to a patient for 1 to 14 days after surgery, and preferably 1 to 3 days after surgery. Thereby, the nutritional status of the patient can be maintained in a healthy state. The dose and the dosing rate can be suitably determined in view of each patient's symptoms, age, and the like. In particular, when the infusion preparation of the present invention is used, the infusion preparation can maintain, by itself, the nutritional status of the patient in a healthy state for the duration of administration.

The infusion preparation of the present invention is preferably administered into a peripheral vein. In other words, the infusion preparation of the present invention is preferably an infusion preparation for peripheral intravenous administration. Usually, when an infusion is administered into a peripheral vein, if the osmotic pressure of the infusion is too high, it may cause vascular pain or phlebitis. However, there is no such risk when the infusion preparation of the present invention is used. Therefore, the effect of the infusion preparation of the present invention is preferably demonstrated when the infusion preparation is administered into a peripheral vein.

Infusion Container

The container in which the first-chamber infusion and the second-chamber infusion are placed is not particularly limited insofar as the container has two chambers that are intercommunicable. Examples include two-chamber containers (infusion bags) in which the chambers are separated by a partition wall that can be communicably opened, such as ones in which a partition wall is formed by an easily peelable seal (Japanese Unexamined Patent Publication No. H2-4671, Japanese Unexamined Utility Model Publication No. H5-5138, and the like); ones in which a partition wall is formed by clipping the space between the chambers (Japanese Unexamined Patent Publication No. S63-309263, and the like); and ones in which various communicating means that can open the partition wall is provided to the partition wall (Japanese Examined Patent Publication No. S63-20550, and the like). Of these, an infusion bag in which the partition wall is formed by an easily peelable seal is preferable because it is suitable for mass production and the chambers can be easily brought into communication. Further, various gas-permeable plastics commonly used for medical containers are used as materials of the above container. Examples include flexible plastics, such as polyethylene, polypropylene, polyvinyl chloride, crosslinked ethylene-vinyl acetate copolymer, ethylene-α-olefin copolymer, blends of such polymers, and laminates comprising such polymers.

The first- and second-chamber infusions can be placed and contained in the container by a conventional method. For example, the chambers are filled with the respective infusions under an inert gas atmosphere, sealed, and sterilized by heat. Heat sterilization can be performed by a known method, such as high-pressure steam sterilization or hot water shower sterilization. If necessary, the heat sterilization can be carried out in an inert gas atmosphere such as carbon dioxide or nitrogen.

Further, the first- and second-chamber infusions contained in the container are preferably packaged together with an oxygen absorber in an oxygen barrier exterior bag, in order to reliably prevent degeneration and oxidation. Particularly when an infusion bag in which the partition wall is formed by an easily peelable seal is used as a container, the infusion bag is preferably packaged in such a manner that the infusion bag is folded, for example, in half, at the easily peelable seal portion so that the partition wall will not be communicably opened by external pressure. Further, for example, the package may be filled with an inert gas if necessary.

Commonly widely used films, sheets, and the like formed from various materials can be used as materials of the oxygen barrier exterior bag, which are suitable for the package. Specific examples include ethylene vinylalcohol copolymer, polyvinylidene chloride, polyacrylonitrile, polyvinyl alcohol, polyamide, and polyester. Examples also include films and sheets formed from materials comprising at least one of the above-mentioned materials.

Further, as the oxygen absorber, various known types can be used. For example, ones comprising, as an active ingredient, an iron compound such as ferric hydroxide, ferric oxide, or iron carbide, and ones comprising low-molecular-weight phenol and activated carbon, can be used. Trade names of typical commercial products include "Ageless" (produced by Mitsubishi Gas Chemical), "Moduran" (produced by Nippon Kayaku), "Secur" (produced by Nippon Soda), "Tamotsu" (produced by Oji Kako), and "Keepit" (produced by Drency).

EXAMPLES

The present invention is described in further detail below in reference to Examples, but is not limited thereto.

Example 1 Formulation of Infusion Preparation

1. Formulation of First-Chamber Infusion

Purified soybean oil, purified egg yolk lecithin, and glucose in the amounts shown in Table 2 were added to water.

The mixture was subjected to crude emulsification using a homomixer. The result was subjected to fine emulsification using a high-pressure emulsifier (Manton-Gaulin), and water was further added thereto to make the total amount 250 mL. The pH was adjusted to about 6.0 using a pH adjuster (L-histidine and hydrochloric acid). The first-chamber infusion thus obtained had a relative osmotic pressure of 3.0, and a titratable acidity of 0.5.

TABLE 2

| Components of First-Chamber Infusion | |
| --- | --- |
| Purified soybean oil | 10 g |
| Glucose | 37.5 g |
| Purified egg yolk lecithin | 1.2 g |
| L-histidine | 0.04 g |

2. Formulation of Second-Chamber Infusion

Amino acids, electrolytes, and a stabilizer (sodium hydrogen sulfite) in the amounts shown in Table 3 were dissolved in distilled water for injection to prepare an amino acid electrolyte solution. The pH of the solution was adjusted to 6.7 with glacial acetic acid, and the total amount was adjusted to 250 mL, giving the second-chamber infusion. The second-chamber infusion thus prepared had a relative osmotic pressure of 3.0 and potassium concentration of 40 mEq/L.

TABLE 3

| Components of Second-Chamber Infusion | |
| --- | --- |
| L-leucine | 2.100 g |
| L-isoleucine | 1.200 g |
| L-valine | 1.200 g |
| L-lysine hydrochloride | 1.965 g |
| L-threonine | 0.855 g |
| L-tryptophan | 0.300 g |
| L-methionine | 0.585 g |
| Acetylcysteine | 0.202 g |
| L-phenylalanine | 1.050 g |
| L-tyrosine | 0.075 g |
| L-arginine | 1.575 g |
| L-histidine | 0.750 g |
| L-alanine | 1.200 g |
| L-proline | 0.750 g |
| L-serine | 0.450 g |
| Glycine | 0.885 g |
| L-asparatic acid | 0.150 g |
| L-glutamic acid | 0.150 g |
| Sodium chloride | 0.220 g |
| Potassium chloride | 0.220 g |
| Sodium citrate | 0.310 g |
| Sodium acetate | 0.403 g |
| Sodium lactate (72% solution) | 1.167 g |
| Potassium glycerophosphate (50% solution) | 1.750 g |
| Calcium gluconate hydrate | 0.561 g |
| Magnesium sulfate hydrate | 0.309 g |
| Zinc sulfate hydrate | 0.70 mg |
| Sodium hydrogen sulfite | 12.5 mg |

3. Filling and Packaging 250 mL of the first-chamber infusion and 250 mL of the second-chamber infusion obtained above were each placed in each chamber of the two-chamber polyethylene container wherein the chambers were partitioned by an easily peelable seal. The atmosphere in the vacant space of each chamber was replaced with nitrogen gas. After sealing, the container was subjected to high-pressure steam sterilization according to a conventional method. Thereafter, the container was folded at the easily peelable seal portion, and enclosed in an exterior bag (oxygen-barrier exterior bag) formed from a multilayered-barrier film (Product name: Bovlon, produced by NSR (Nippon Synthetic Chemical Industry Co., Ltd.) together with a deoxidant (Product name: Ageless, produced by Mitsubishi Gas Chemical Company, Inc.), obtaining an infusion preparation. Note that the mixture (the components are shown in Table 4) of the first-chamber infusion and the second-chamber infusion of the infusion preparation had a pH of 6.7, a titratable acidity of 7, and a potassium concentration of 20 mEq/L. During storage for 3 days from the time of mixing, the mixed infusion exhibited a volume ratio of coarse particles having a particle size of 0.5 μm or more of 0.05% or less, which was lower than the requirements of the United States Pharmacopeia (USP), indicating that the fat particles thereof were stable. The particle size was measured using AccuSizer 780 (produced by Perticle Sizing System).

TABLE 4

| Components of Mixed Infusion | | |
| --- | --- | --- |
| | Components | Amount (500 mL) |
| Sugar | Glucose | 37.5 g |
| Fat | Soybean oil | 10 g |
| Amino acids | L-leucine | 2.100 g |
| | L-isoleucine | 1.200 g |
| | L-valine | 1.200 g |
| | L-lysine hydrochloride | 1.965 g |
| | L-threonine | 0.855 g |
| | L-tryptophan | 0.300 g |
| | L-methionine | 0.585 g |
| | Acetylcysteine | 0.202 g |
| | L-phenylalanine | 1.050 g |
| | L-tyrosine | 0.075 g |
| | L-arginine | 1.575 g |
| | L-histidine | 0.790 g |
| | L-alanine | 1.200 g |
| | L-proline | 0.750 g |
| | L-serine | 0.450 g |
| | Glycine | 0.885 g |
| | L-asparatic acid | 0.150 g |
| | L-glutamic acid | 0.150 g |
| Electrolytes | Na | 17.5 mEq |
| | K | 10 mEq |
| | Mg | 2.5 mEq |
| | Ca | 2.5 mEq |
| | Cl | 17.5 mEq |
| | P | 5 mmol |
| | Zn | 2.5 μmol |

Example 2 Formulation of Infusion Preparation

1. Formulation of First-Chamber Infusion 250 mL of a fluid comprising 0.96 mg of thiamine chloride hydrochloride in addition to the components shown in Table 2 was prepared in the same manner as in Example 1 to obtain a first-chamber infusion. The pH of the first-chamber infusion was adjusted to about 6.0. The first-chamber infusion had a relative osmotic pressure of 3 and a titratable acidity of 0.5.

2. Formulation of Second-Chamber Infusion

A second-chamber infusion was prepared in the same manner as in Example 1.

3. Filling and Packaging 250 mL of the first-chamber infusion and 250 mL of the second-chamber infusion obtained above were each placed in each chamber of the two-chamber polyethylene container wherein the chambers were partitioned by an easily peelable seal. The atmosphere in the vacant space of each chamber was replaced with nitrogen gas. After sealing, the container was subjected to high-pressure steam sterilization according to a conventional method. Thereafter, the container was folded at the easily peelable seal portion, and enclosed in an exterior bag (oxygen-barrier exterior bag) formed from a multilayered-barrier film (Product name: Bovlon, produced by NSR) together with a deoxidant (Product name: Ageless, produced by Mitsubishi Gas Chemical Company, Inc.), obtaining an infusion preparation. Note that the mixture (the components are shown in Table 5) of the first-chamber infusion and the second-chamber infusion of the infusion preparation had a pH of 6.7, a titratable acidity of 7, and a potassium concentration of 20 mEq/L. During storage for 3 days from the time of mixing, the mixed infusion exhibited a volume ratio of coarse particles having a particle size of 0.5 μm or more of 0.05% or less, indicating that the fat particles thereof were stable.

TABLE 5

Components of Mixed Infusion

|  | Components | Amount (500 mL) |
|---|---|---|
| Sugar | Glucose | 37.5 g |
| Fat | Soybean oil | 10 g |
| Amino acids | L-leucine | 2.100 g |
|  | L-isoleucine | 1.200 g |
|  | L-valine | 1.200 g |
|  | L-lysine hydrochloride | 1.965 g |
|  | L-threonine | 0.855 g |
|  | L-tryptophan | 0.300 g |
|  | L-methionine | 0.585 g |
|  | Acetylcysteine | 0.202 g |
|  | L-phenylalanine | 1.050 g |
|  | L-tyrosine | 0.075 g |
|  | L-arginine | 1.575 g |
|  | L-histidine | 0.790 g |
|  | L-alanine | 1.200 g |
|  | L-proline | 0.750 g |
|  | L-serine | 0.450 g |
|  | Glycine | 0.885 g |
|  | L-asparatic acid | 0.150 g |
|  | L-glutamic acid | 0.150 g |
| Electrolytes | Na | 17.5 mEq |
|  | K | 10 mEq |
|  | Mg | 2.5 mEq |
|  | Ca | 2.5 mEq |
|  | Cl | 17.5 mEq |
|  | P | 5 mmol |
|  | Zn | 2.5 μmol |
| Vitamins | Thiamine chloride hydrochloride | 0.96 mg |

Example 3 Formulation of Infusion Preparation

1. Formulation of First-Chamber Infusion 250 mL of fluid comprising 2.75 mg of vitamin A oil (825 IU), 1.25 μg of cholecalciferol, 2.5 mg of tocopherol acetate, 1 mg of phytonadione, 0.96 mg of thiamine chloride hydrochloride, 1.23 mg of pyridoxine hydrochloride, 1.25 μg of cyanocobalamin, and 0.1 mg of folic acid in addition to the components shown in Table 2 was prepared in the same manner as in Example 1 to obtain a first-chamber infusion. The vitamin A oil, cholecalciferol, tocopherol acetate, and phytonadione were dissolved in the purified soybean oil beforehand. The pH of the first-chamber infusion was adjusted to about 6.0. The first-chamber infusion had a relative osmotic pressure of 3.0 and a titratable acidity of 0.5.

2. Formulation of Second-Chamber Infusion 250 mL of fluid comprising 25 mg of ascorbic acid, 15 μg of biotin, 10 mg of nicotinamide, 3.5 mg of panthenol, and 1.15 mg of riboflavin sodium phosphate in addition to the components shown in Table 3 was prepared in the same manner as in Example 1 to obtain a second-chamber infusion. The second-chamber infusion had a relative osmotic pressure of 3 and a potassium concentration of 40 mEq/L. The pH of the second-chamber infusion was adjusted to 6.7.

3. Filling and Packaging 250 mL of the first-chamber infusion and 250 mL of the second-chamber infusion obtained above were each placed in each chamber of the two-chamber polyethylene container wherein the chambers were partitioned by an easily peelable seal. The atmosphere in the vacant space of each chamber was replaced with nitrogen gas. After sealing, the container was subjected to high-pressure steam sterilization according to a conventional method. Thereafter, the container was folded at the easily peelable seal portion, and enclosed in an exterior bag (oxygen-barrier exterior bag) formed from a multilayered-barrier film (Product name: Bovlon, produced by NSR) together with a deoxidant (Product name: Ageless, produced by Mitsubishi Gas Chemical Company, Inc.), obtaining an infusion preparation. Note that the mixture (the components are shown in Table 6) of the first-chamber infusion and the second-chamber infusion of the infusion preparation had a pH of 6.7, a titratable acidity of 7, and a potassium concentration of 20 mEq/L. During storage for 3 days from the time of mixing, the mixed infusion exhibited a volume ratio of coarse particles having a particle size of 0.5 μm or more of 0.05% or less, indicating that the fat particles thereof were stable.

TABLE 6

Components of Mixed Infusion

|  | Components | Amount (500 mL) |
|---|---|---|
| Sugar | Glucose | 37.5 g |
| Fat | Soybean oil | 10 g |
| Amino acids | L-leucine | 2.100 g |
|  | L-isoleucine | 1.200 g |
|  | L-valine | 1.200 g |
|  | L-lysine hydrochloride | 1.965 g |
|  | L-threonine | 0.855 g |
|  | L-tryptophan | 0.300 g |
|  | L-methionine | 0.585 g |
|  | Acetylcysteine | 0.202 g |
|  | L-phenylalanine | 1.050 g |
|  | L-tyrosine | 0.075 g |
|  | L-arginine | 1.575 g |
|  | L-histidine | 0.790 g |
|  | L-alanine | 1.200 g |
|  | L-proline | 0.750 g |
|  | L-serine | 0.450 g |
|  | Glycine | 0.885 g |
|  | L-asparatic acid | 0.150 g |
|  | L-glutamic acid | 0.150 g |
| Electrolytes | Na | 17.5 mEq |
|  | K | 10 mEq |
|  | Mg | 2.5 mEq |
|  | Ca | 2.5 mEq |
|  | Cl | 17.5 mEq |
|  | P | 5 mmol |
|  | Zn | 2.5 μmol |
| Vitamins | Thiamine chloride hydrochloride | 0.96 mg |
|  | Riboflavin sodium phosphate | 1.15 mg |
|  | Pyridoxine hydrochloride | 1.23 mg |
|  | Cyanocobalamin | 1.25 μg |
|  | Nicotinamide | 10 mg |
|  | Panthenol | 3.5 mg |
|  | Folic acid | 0.10 mg |
|  | Biotin | 15 μg |
|  | Ascorbic acid | 25 mg |
|  | Vitamin A oil | 825 IU |
|  | Cholecalciferol | 1.25 μg |
|  | Tocopherol acetate | 2.5 mg |
|  | Phytonadione | 1 mg |

The infusion preparation (before mixing the first-chamber infusion and the second-chamber infusion) was stored at room temperature for 6 months. Thereafter, the amount of each vitamin component contained in the first-chamber infusion or the second-chamber infusion was measured using HPLC. Table 7 shows the results. As is clear from the results, each of the vitamin components can be stably present in the infusion preparation even after 6 months storage.

TABLE 7

| Remaining rate after 6 months storage (%) | |
| --- | --- |
| Riboflavin sodium phosphate | 100.1 |
| Ascorbic acid | 99.9 |
| Biotin | 97.8 |
| Nicotinamide | 99.6 |
| Panthenol | 100.4 |
| Thiamine chloride hydrochloride | 98.7 |
| Pyridoxine hydrochloride | 99.3 |
| Cyanocobalamin | 103.2 |
| Folic acid | 100.0 |
| Cholecalciferol | 100.5 |
| Tocopherol acetate | 99.0 |
| Phytonadione | 101.5 |
| Vitamin A oil | 102.2 |

Example 4 Formulation of Infusion Preparation

1. Formulation of First-Chamber Infusion 300 mL of fluid comprising 2.75 mg of vitamin A oil (825 IU), 1.25 μg of cholecalciferol, 2.5 mg of tocopherol acetate, 37.55 μg of phytonadione, 1.92 mg of thiamine chloride hydrochloride, 1.82 mg of pyridoxine hydrochloride, 1.25 μg of cyanocobalamin, and 0.15 mg of folic acid in addition to the components shown in Table 2 was prepared in the same manner as in Example 3 to obtain a first-chamber infusion. The pH of the first-chamber infusion was adjusted to about 6.0. The first-chamber infusion had a relative osmotic pressure of 2.5 and a titratable acidity of 0.5.

2. Formulation of Second-Chamber Infusion 250 mL of fluid comprising 50 mg of vitamin C (ascorbic acid), 15 μg of biotin, 10 mg of nicotinamide, 3.5 mg of panthenol, and 1.15 mg of vitamin B2 (riboflavin sodium phosphate) was prepared in the same manner as in Example 3 to obtain a second-chamber infusion. The pH of the second-chamber infusion was adjusted to 6.7. The second-chamber infusion had a relative osmotic pressure of 3.0 and a potassium concentration of mEq/L.

3. Filling and Packaging 300 mL of the first-chamber infusion and 250 mL of the second-chamber infusion obtained above were each placed in each chamber of the two-chamber polyethylene container wherein the chambers were partitioned by an easily peelable seal. The atmosphere in the vacant space of each chamber was replaced with nitrogen gas. After sealing, the container was subjected to high-pressure steam sterilization according to a conventional method. Thereafter, the container was folded at the easily peelable seal portion, and enclosed in an exterior bag (oxygen-barrier exterior bag) formed from a multilayered-barrier film (Product name: Bovlon, produced by NSR) together with a deoxidant (Product name: Ageless, produced by Mitsubishi Gas Chemical Company, Inc.), obtaining an infusion preparation. Note that the mixture (the components are shown in Table 8) of the first-chamber infusion and the second-chamber infusion of the infusion preparation had a pH of 6.7, a titratable acidity of 6, and a potassium concentration of 18.2 mEq/L. During storage for 3 days from the time of mixing, the mixed infusion exhibited a volume ratio of coarse particles having a particle size of 0.5 μm or more of 0.05% or less, indicating that the fat particles thereof were stable.

TABLE 8

| Components of Mixed Infusion | | |
| --- | --- | --- |
| | Components | Amount (550 mL) |
| Sugar | Glucose | 37.5 g |
| Fat | Soybean oil | 10 g |
| Amino acids | L-leucine | 2.100 g |
| | L-isoleucine | 1.200 g |
| | L-valine | 1.200 g |
| | L-lysine hydrochloride | 1.965 g |
| | L-threonine | 0.855 g |
| | L-tryptophan | 0.300 g |
| | L-methionine | 0.585 g |
| | Acetylcysteine | 0.202 g |
| | L-phenylalanine | 1.050 g |
| | L-tyrosine | 0.075 g |
| | L-arginine | 1.575 g |
| | L-histidine | 0.790 g |
| | L-alanine | 1.200 g |
| | L-proline | 0.750 g |
| | L-serine | 0.450 g |
| | Glycine | 0.885 g |
| | L-asparatic acid | 0.150 g |
| | L-glutamic acid | 0.150 g |
| Electrolytes | Na | 17.5 mEq |
| | K | 10 mEq |
| | Mg | 2.5 mEq |
| | Ca | 2.5 mEq |
| | Cl | 17.5 mEq |
| | P | 5 mmol |
| | Zn | 2.5 μmol |
| Vitamins | Thiamine chloride hydrochloride | 1.92 mg |
| | Riboflavin sodium phosphate | 1.15 mg |
| | Pyridoxine hydrochloride | 1.82 mg |
| | Cyanocobalamin | 1.25 μg |
| | Nicotinamide | 10 mg |
| | Panthenol | 3.5 mg |
| | Folic acid | 0.15 mg |
| | Biotin | 15 μg |
| | Ascorbic acid | 50 mg |
| | Vitamin A oil | 825 IU |
| | Cholecalciferol | 1.25 μg |
| | Tocopherol acetate | 2.5 mg |
| | Phytonadione | 37.5 μg |

Comparative Example 1

Formulation of Infusion Preparation

1. Formulation of First-Chamber Infusion

Purified soybean oil, purified egg yolk lecithin, and glucose in the amounts shown in Table 2 were added to water. The mixture was subjected to crude emulsification using a homomixer. The result was subjected to fine emulsification using a high-pressure emulsifier (Manton-Gaulin), and water was added thereto to make the total amount 350 mL. The pH was adjusted to about 6.0 using a pH adjuster (L-histidine and hydrochloric acid). The first-chamber infusion thus obtained had a relative osmotic pressure of 2.1, and a titratable acidity of 0.5.

2. Formulation of Second-Chamber Infusion 150 mL of fluid comprising the components shown in Table 3 was prepared in the same manner as in Example 1 to obtain a second-chamber infusion. The pH of the second-chamber infusion was adjusted to 6.7. The second-chamber infusion had a relative osmotic pressure of 5 and a potassium concentration of 67 mEq/L.

3. Filling and Packaging 350 mL of the first-chamber infusion and 150 mL of the second-chamber infusion obtained above were each placed in each chamber of the two-chamber polyethylene container wherein the chambers were partitioned by an easily peelable seal. The atmosphere in the vacant space of each chamber was replaced with nitrogen gas. After sealing, the container was subjected to high-pressure steam sterilization according to a conventional method. Thereafter, the container was folded at the easily peelable seal portion, and enclosed in an exterior bag (oxygen-barrier exterior bag) formed from a multilayered-barrier film (Product name: Bovlon, produced by NSR) together with a deoxidant (Product name: Ageless, produced by Mitsubishi Gas Chemical Company, Inc.), obtaining an infusion preparation. The mixed infusion of the first-chamber infusion and the second-chamber infusion of the infusion preparation, comprised the same components at the same proportions as that in Example 1. However, in the formulation of Comparative Example 1, the second-chamber infusion had a high potassium concentration of 67 mEq/L; therefore, if the infusion preparation were used before opening the partition, a high concentration of potassium would undesirably be administered into the body, thus making it extremely dangerous. Furthermore, the relative osmotic pressure in the second chamber was very high at and adverse effects such as phlebitis caused thereby cannot be neglected.

The invention claimed is:

1. An infusion preparation comprising two chambers separated by a partition that can be communicably opened, wherein
 a first chamber contains a first-chamber infusion comprising a sugar and a fat emulsion;
 a second chamber contains a second-chamber infusion comprising an amino acid and an electrolyte;
 the first-chamber infusion is substantially free of potassium, and has a relative osmotic pressure of 2.0 to 3.0;
 the second-chamber infusion has a potassium concentration of 40 mEq/L or less and a relative osmotic pressure of 2.5 to 3.5;
 and a mixture of the first- and second-chamber infusions has a potassium concentration of 16 mEq/L or more as measured upon communicably opening the partition; and
 the volume ratio of the first-chamber infusion to the second-chamber infusion is 3:2 to 3:3.

2. The infusion preparation according to claim 1 wherein the first-chamber infusion has a pH of 4.5 to 6.5, and the second-chamber infusion has a pH of 6.0 to 7.4.

3. The infusion preparation according to claim 1, wherein the first chamber further contains vitamin B1.

4. The infusion preparation according to claim 2, wherein the first chamber further contains vitamin B1.

5. The infusion preparation according to claim 3, wherein the first-chamber infusion further contains vitamin A, vitamin B6, vitamin B12, vitamin D, vitamin E, and vitamin K, and the second-chamber infusion further contains vitamin C and vitamin B2.

6. The infusion preparation according to claim 4, wherein the first-chamber infusion further contains vitamin A, vitamin B6, vitamin B12, vitamin D, vitamin E, and vitamin K, and the second-chamber infusion further contains vitamin C and vitamin B2.

* * * * *